United States Patent
Suzuki et al.

(10) Patent No.: US 11,933,706 B2
(45) Date of Patent: Mar. 19, 2024

(54) METHOD OF ANALYZING METAL COMPONENT AND METHOD OF MANUFACTURING PURIFIED POLYMER PRODUCT

(71) Applicant: TOKYO OHKA KOGYO CO., LTD., Kanagawa (JP)

(72) Inventors: Kohei Suzuki, Kawasaki (JP); Isao Nouchi, Kawasaki (JP); Toshio Nomura, Kawasaki (JP)

(73) Assignee: TOKYO OHKA KOGYO CO., LTD., Kanagawa (JP)

( * ) Notice: Subject to any disclaimer, the term of this patent is extended or adjusted under 35 U.S.C. 154(b) by 289 days.

(21) Appl. No.: 17/215,711

(22) Filed: Mar. 29, 2021

(65) Prior Publication Data
US 2021/0310911 A1 Oct. 7, 2021

(30) Foreign Application Priority Data
Apr. 1, 2020 (JP) .................... 2020-065652

(51) Int. Cl.
*G01N 1/38* (2006.01)
*G01N 27/623* (2021.01)
*G01N 33/44* (2006.01)
*H01J 49/10* (2006.01)

(52) U.S. Cl.
CPC .......... *G01N 1/38* (2013.01); *G01N 27/623* (2021.01); *G01N 33/442* (2013.01); *H01J 49/105* (2013.01); *G01N 2001/383* (2013.01)

(58) Field of Classification Search
CPC ...... G01N 1/38; G01N 27/623; G01N 33/442; G01N 2001/383; H01J 49/105
See application file for complete search history.

(56) References Cited

U.S. PATENT DOCUMENTS 4,992,529 A * 2/1991 Hoxmeier ............. C08F 6/02
528/487
2017/0256388 A1 9/2017 Taniguchi

FOREIGN PATENT DOCUMENTS

| JP | 63-126502 | | 5/1988 |
|---|---|---|---|
| JP | 2001-215217 | | 8/2001 |
| JP | 2006-184109 | | 7/2006 |
| JP | 2006184109 A | * | 7/2006 |
| JP | 2017-156332 | | 9/2017 |

* cited by examiner

*Primary Examiner* — Jill A Warden
*Assistant Examiner* — Alex Ramirez
(74) *Attorney, Agent, or Firm* — WENDEROTH, LIND & PONACK, L.L.P.

(57) ABSTRACT

A method of analyzing a metal component contained as an impurity in a polymer composition that contains a polymer and an organic solvent including a step (i) of preparing a dispersion by mixing the polymer composition with an acid aqueous solution, a step (ii) of separating the dispersion prepared in the step (i) into a dispersoid layer containing the polymer and a dispersion medium layer containing the metal component, and a step (iii) of quantifying the metal component contained in the dispersion medium layer separated in the step (ii).

3 Claims, 1 Drawing Sheet

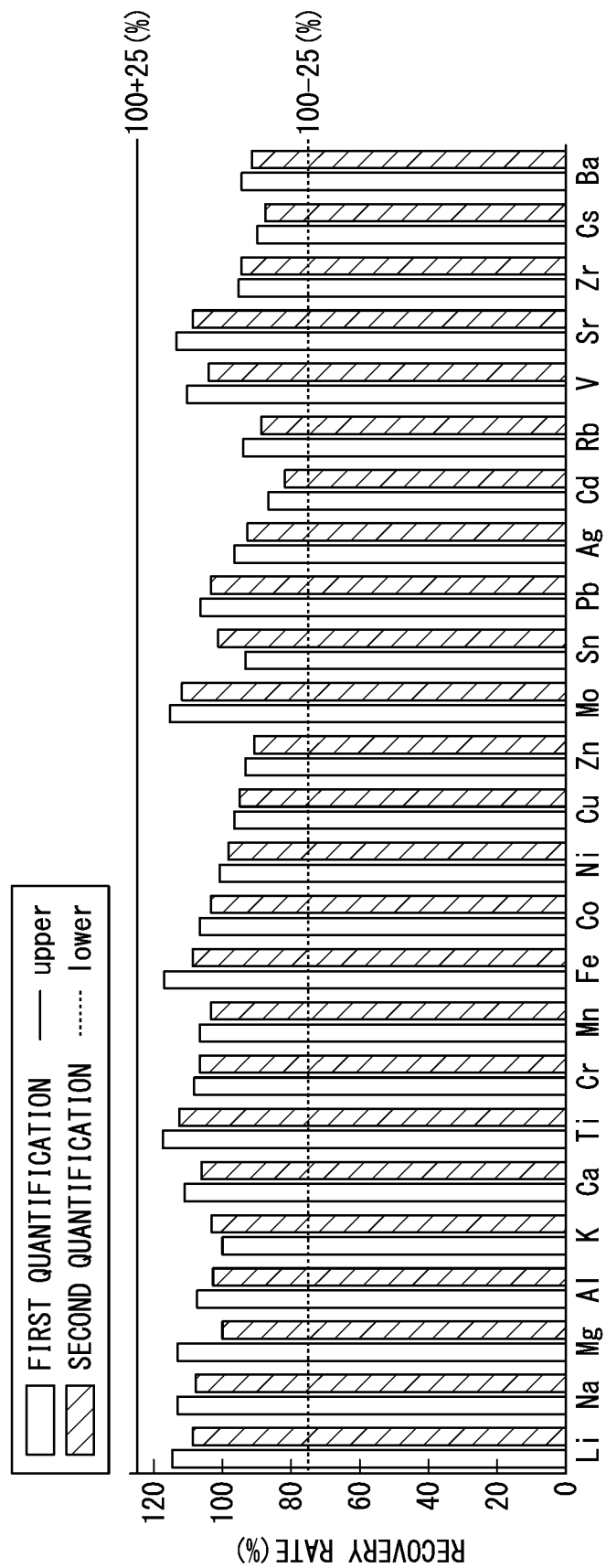

METHOD OF ANALYZING METAL COMPONENT AND METHOD OF MANUFACTURING PURIFIED POLYMER PRODUCT

BACKGROUND OF THE INVENTION

Field of the Invention

The present invention relates to a method of analyzing a metal component and a method of manufacturing a purified polymer product.

Description of Related Art

In lithography technology, for example, a method of forming a resist film made of a resist material on a substrate, exposing the resist film selectively, and performing a development process to form a resist pattern having a predetermined shape on the resist film is used.

In the manufacture of semiconductor devices or liquid crystal display devices, patterns are miniaturized and the substrate is more multilayered, rapidly, due to the progress of the lithography technology. Along with this, there is an increasing demand for removing foreign substances (impurities) mixed in the resist material.

In particular, there is a problem that metal components (metal impurities) contained as impurities deteriorate the electrical characteristics of semiconductor devices and the like. In addition, there is also a risk that metal impurities may cause defects. Therefore, it is important to control a concentration of metal components contained in the resist material as impurities.

In the related art, as a method of analyzing metal impurities in a resist material, a dilution method is used in pretreatment such as quantification.

For example, a method in which a solid polymer is dissolved in an organic solvent to obtain a polymer solution, the polymer solution is then directly introduced into an inductively coupled plasma mass spectrometer (ICP-MS) to analyze a concentration of metal elements in the solid polymer (see Patent Literature 1).

DOCUMENTS OF RELATED ART

Patent Literature

[Patent Literature 1] Japanese Unexamined Patent Application, First Publication No. 2006-184109

SUMMARY OF THE INVENTION

In recent years, with further miniaturization of patterns and multilayered substrates, a demand for the reduction of metal impurities contained in resist materials is more stringent in a manufacturing process of semiconductors or the like.

On the other hand, there is a need for a method capable of analyzing a metal component whose concentration of a detection limit (DL) is lower than that of the analysis method in the related art, and who presents in the resist material by trace amount.

The present invention has been made in view of the above circumstances, and an object of the present invention is to provide a method of analyzing a metal component, which can lower the most minimum limit capable of being quantified. Another object of the present invention is to provide a method of manufacturing a purified polymer product in which metal impurities are further reduced.

According to the studies, the present inventors have found that a detection limit (DL) is 2 digits ppt in a case where a dilution method in the related art is adopted for the pretreatment in the method of analyzing metal impurities in a polymer composition containing a polymer and an organic solvent, but the detection limit (DL) can be lowered to a single-digit ppt, particularly 5 ppt or less by adopting a liquid-liquid extraction method, and as a result the present inventors have completed the present invention.

That is, one aspect of the present invention is a method of analyzing a metal component contained as an impurity in a polymer composition that contains a polymer and an organic solvent including a step (i) of preparing a dispersion by mixing the polymer composition with an acid aqueous solution, a step (ii) of separating the dispersion into a dispersoid layer containing the polymer and a dispersion medium layer containing the metal component, and a step (iii) of quantifying the metal component contained in the dispersion medium layer.

Another aspect of the present invention is a method of manufacturing a purified polymer product including a step (I) of preparing a dispersion by mixing a polymer composition containing a polymer, an organic solvent, and metal impurities with an acid aqueous solution, a step (II) of separating the dispersion into a dispersoid layer containing the polymer and a dispersion medium layer containing the metal impurities, and a step (III) of recovering the polymer contained in the dispersoid layer to obtain a purified polymer product.

According to the method of analyzing a metal component according to one aspect of the present invention, the most minimum limit capable of being quantified can be further lowered, and a detection limit (DL) of 5 ppt or less for each metal element species in the polymer composition can be realized.

Furthermore, in the manufacturing method according to another aspect of the present invention, it is possible to manufacture the purified polymer product having further reduced metal impurities.

BRIEF DESCRIPTION OF THE DRAWINGS

FIG. 1 is a graph showing the results of an addition recovery test. The vertical axis represents a recovery rate (%). The horizontal axis represents each metal element. The results of quantification twice are shown for one metal element.

DETAILED DESCRIPTION OF THE INVENTION (Method of Analyzing Metal Component)

In the present embodiment, a method of analyzing a metal component that is contained as an impurity in a polymer composition containing a polymer and an organic solvent includes the following step (i), step (ii), and step (iii).

Step (i): a step (i) of preparing a dispersion by mixing the polymer composition with an acid aqueous solution.

Step (ii): a step (ii) of separating the dispersion into a dispersoid layer containing the polymer and a dispersion medium layer containing the metal component.

Step (iii): a step (iii) of quantifying the metal component contained in the dispersion medium layer.

The polymer composition in the present embodiment is not particularly limited as long as the polymer composition contains a polymer and an organic solvent, and examples thereof include a resist composition and a coating material.

In particular, in a case where a resist composition for which there is a strict requirement for reduction of metal impurities is subjected to an analysis, the method of analyzing a metal component of the present embodiment is useful.

Exemplary examples of the polymer include polyester-based resins, polyamide-based resins, polyurethane-based resins, epoxy-based resins, phenol-based resins, acrylic-based resins, polyvinyl acetate-based resins, cellulose-based resins, styrene-based resins, hydroxystyrene-based resins, and copolymer resins thereof.

The organic solvent may be any organic solvent that can dissolve a polymer, and exemplary examples thereof include lactones, ketones, polyhydric alcohols; compounds having an ester bond such as ethylene glycol monoacetate, diethylene glycol monoacetate, propylene glycol monoacetate, and dipropylene glycol monoacetate; derivatives of polyhydric alcohols such as compounds having an ether bond such as monophenyl ethers or monoalkyl ethers such as monomethyl ether, monoethyl ether, monopropyl ether, and monobutyl ether of the polyhydric alcohols or the compounds having the ester bond (among these, propylene glycol monomethyl ether acetate (PGMEA) and propylene glycol monomethyl ether (PGME) are preferable); cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic organic solvents, dimethyl sulfoxide, and the like.

Exemplary examples of the metal component contained as an impurity in the polymer composition in the present embodiment include lithium, sodium, magnesium, aluminum, potassium, calcium, titanium, chromium, manganese, iron, cobalt, nickel, copper, zinc, molybdenum, tin, lead, silver, cadmium, rubidium, vanadium, strontium, zirconium, cesium, barium, germanium, tungsten, and the like.

Hereinafter, the step (i), step (ii), and step (iii) will be described.

As an example, resist materials used in the manufacture of semiconductor devices and liquid crystal display devices are strictly controlled for metal impurities. Therefore, the concentration of metal components contained as impurities in the polymer composition subjected to be analyzed is often several ppb or less for each metal element species at the time of the pretreatment of an analysis.

Therefore, the operation of each step in the present embodiment is usually performed at room temperature (20° C. to 25° C.), and preferably performed in a clean room.

Regarding containers, lids, pipettes, and other instruments, it is preferable to use pre-acid-cleaned instruments from the viewpoint of preventing metal contamination.

<Step (i)>

In the step (i) of the present embodiment, a dispersion is prepared by mixing the polymer composition with an acid aqueous solution.

For example, from the viewpoint of preventing metal contamination, a predetermined amount of each of the polymer composition and the acid aqueous solution is collected in a pre-acid-cleaned container.

In the present embodiment, the polymer composition from a low viscosity to a high viscosity may be subjected to the analysis.

A solid content (components other than a solvent) concentration of the polymer composition is preferably 0.1% to 80% by mass with respect to the total mass (100% by mass) of the polymer composition.

In the present embodiment, the acid aqueous solution refers to a liquid obtained by dissolving at least one or more acids in water.

The acid may be an inorganic acid or an organic acid, and among these, an inorganic acid is preferable. Exemplary examples of the acid include nitric acid, hydrochloric acid, sulfuric acid, hydrogen fluoride, phosphoric acid, perchloric acid, acetic acid, formic acid, and mixed acids containing two or more thereof. Examples of the mixed acids include mixed acids of hydrochloric acid and nitric acid. Further, the acid may be a mixture of hydrochloric acid and hydrogen peroxide.

The acid aqueous solution is preferably a liquid obtained by dissolving at least one selected from the group consisting of nitric acid, hydrochloric acid, sulfuric acid, and hydrogen fluoride in water from the viewpoint of high extractability of a metal component from the polymer composition, and more preferably a liquid obtained by dissolving at least nitric acid in water.

An acid concentration in the acid aqueous solution is, for example, preferably 0.1% to 20% by mass, more preferably 0.2% to 10% by mass, even more preferably 0.3% to 5% by mass, and particularly preferably 0.5% to 1.5% by mass.

The acid aqueous solution in the present embodiment may contain a solvent other than water.

Exemplary examples of the solvent other than water include a solvent that is soluble in water, and for example, alcohol, ketone, ester, and the like are exemplary examples.

A content of the solvent other than water is preferably 20% by mass or less with respect to the total mass (100% by mass) of the acid aqueous solution.

A mixing ratio of the polymer composition to the acid aqueous solution in the step (i) may be determined according to kinds of polymers, the concentration of acids, or the like, and for example, the polymer composition/the acid aqueous solution is preferably 0.80 to 1.25 in terms of a mass ratio.

As long as the mass ratio is within the above preferable range, both the polymer composition and the acid aqueous solution may have the same amount (the mass ratio of 1.0), the polymer composition may have a larger amount (1.0<mass ratio≤1.25) than that of the acid aqueous solution, or the acid aqueous solution may have a larger amount (0.80≤mass ratio<1.0) than that of the polymer composition.

Since the mass ratio is within the above preferable range, the percentage of the polymer composition in dispersion is increased as compared with the case where a dilution method in the related art is adopted, and a concentration of metal impurities is made higher.

The method of mixing the polymer composition with the acid aqueous solution is not particularly limited, but from the viewpoint of preventing metal contamination, the polymer composition and the acid aqueous solution are collected into containers that are covered, and the mixing is performed while rotating each container.

<Step (ii)>

In the step (ii) of the present embodiment, the dispersion prepared in the step (i) is separated into a dispersoid layer containing the polymer and a dispersion medium layer containing the metal component.

Exemplary examples of the separating operation in the step (ii) include centrifugation, filtration, and leaving it to stand for a long time. From the viewpoint of preventing metal contamination and improving efficiency, it is preferable to perform the separating operation by centrifugation. In the case of the operation of centrifugation, the container used in the step (i) can be set in the centrifuge as it is.

A state of the dispersion after the separating operation differs depending on the type of the organic solvent in the polymer composition, and the like, but the dispersion is separated into a dispersoid layer containing the polymer and a dispersion medium layer containing the metal component.

For example, the dispersion is separated into the dispersoid layer and the dispersion medium layer, and the dispersoid layer is precipitated. Alternatively, the dispersion is separated into the dispersoid layer and the dispersion medium layer, the dispersoid layer is precipitated, and the dispersion medium layer is formed into two layers (an aqueous layer and an organic solvent layer).

In any state of layer separated, the metal impurities extracted from the polymer composition are dissolved in the dispersion medium layer (aqueous layer) (this validity is confirmed in <Validity Evaluation of Analysis Method> described later).

<Step (iii)>

In the step (iii) of the present embodiment, the metal component contained in the dispersion medium layer separated in the step (ii) is quantified.

For example, from the dispersion separated into the dispersoid layer and the dispersion medium layer in the step (ii), the dispersion medium layer is collected in a pre-acid-cleaned container.

The method of quantifying the metal component contained in the dispersion medium layer is not particularly limited, and exemplary examples thereof include a method using inductively coupled plasma (ICP), atomic absorption spectroscopy, and the like.

In the present embodiment, since a plurality of types of an elemental analysis can be performed at one time, it is preferable to perform the operation of quantifying the metal component in the step (iii) by a method using ICP.

Exemplary examples of the method using ICP include an ICP emission spectroscopic analysis and an ICP mass spectrometry. Among these, it is preferable to perform the ICP mass spectrometry (ICP-MS) since an ultrasensitive analysis at a single-digit ppt level is possible.

The quantification of each of the metal component obtained by the ICP emission spectroscopic analysis and the ICP mass spectrometry can be performed by known methods.

According to the method of analyzing a metal component of the present embodiment described above, that is, the analysis method including the above step (i), step (ii), and step (iii), the most minimum limit capable of being quantified for the metal component contained as an impurity in the polymer composition can be further lowered. Specifically, it is possible to realize a detection limit (DL) of 5 ppt or less for each metal element species in the polymer composition.

In the present embodiment, as a method of extracting a metal component contained as an impurity from the polymer composition, a liquid-liquid extraction using the polymer composition and the acid aqueous solution in combination is adopted. As a result, in the present embodiment, a large amount of the metal component contained as an impurity can be extracted from the polymer composition as compared with the dilution method using an organic solvent in the related art.

In addition, during the quantification of the metal component, the minimum limit of quantification is at a ppt level. Therefore, from the viewpoint of the detection ability of an analyzer, it is preferable that a concentration of the metal component in the sample solution after the pretreatment is not lowered, and the polymer composition is not diluted as much as possible. In the present embodiment, a dilution magnification of the polymer composition can be reduced by adopting the liquid-liquid extraction. Therefore, the concentration of the metal component in the sample solution used for quantifying the metal component can be increased as compared with the dilution method using an organic solvent in the related art.

The method of analyzing a metal component according to the above described embodiment includes the step (i), the step (ii), and the step (iii), but the present invention is not limited thereto, and the method may include other steps. For example, a step (concentration step) of concentrating the dispersion medium layer may be provided between the step (ii) and the step (iii) in order to further increase the concentration of the metal component in the sample solution.

In a case of providing other steps, it is necessary to pay attention to metal contamination.

According to the present embodiment, even in the method including the above described step (i), step (ii), and step (iii), the detection limit (DL) for each metal element species in the polymer composition can be lowered to a single-digit ppt, in particular 5 ppt or less.

The method of analyzing a metal component according to the above described embodiment can be widely used in an industrial field in which a polymer composition containing a polymer and an organic solvent is used. For example, the method of analyzing a metal component according to an embodiment can be suitably used in a step (inspection step) that is included in a method of manufacturing a resist material used in the manufacture of a semiconductor and the like, particularly a resist composition for which there is a strict requirement for reduction of metal impurities.

Specifically, in the inspection step, by comparing the specified value of each metal element species with the analysis result of the metal component in the polymer composition as a sample, a polymer composition in which all the metal element species have a specified value or less is determined as a "product", and a polymer composition containing the metal element species that has a value exceeds the specified value is determined as "not a product".

(Method of Manufacturing Purified Polymer Product)

A method of manufacturing a purified polymer product of the present embodiment includes a step (I) of preparing a dispersion by mixing a polymer composition containing a polymer, an organic solvent, and metal impurities with an acid aqueous solution, a step (II) of separating the dispersion into a dispersoid layer containing the polymer and a dispersion medium layer containing the metal impurities, and a step (III) of recovering the polymer contained in the dispersoid layer to obtain a purified polymer product.

The description of each of the step (I) and the step (II) in the present embodiment is the same as each of the step (i) and step (ii) described above.

In the step (III) of the present embodiment, the polymer contained in the dispersoid layer separated in the step (II) is recovered to obtain a purified polymer product.

For example, the dispersoid layer that is being precipitated is collected and recovered from the dispersion separated into the dispersoid layer and the dispersion medium layer in the step (II), and washed to obtain the purified polymer product.

According to the method of manufacturing a purified polymer product of the present embodiment described above, it is possible to manufacture the purified polymer product having further reduced metal impurities. For example, by blending this purified polymer product with a resist composition, it is possible to improve and stabilize the electrical characteristics of a semiconductor device or the like. In addition, an occurrence of defects is suppressed in pattern formation.

EXAMPLE

Hereinafter, the present invention will be described in more detail with reference to Examples, but the present invention is not limited to these examples.

<Validity Evaluation of Analysis Method>

The following polymer compositions, acid aqueous solutions, and metal reagents were used.

As the polymer composition, a first resist composition described in Japanese Unexamined Patent Application, First Publication No. 2016-075904 was used as follows.

First resist composition: Positive resist composition containing 100 parts by mass of a polymer compound as a base material component, 10.1 parts by mass of a photoacid generator component, 2.0 parts by mass of salicylic acid, 7.29 parts by mass of a base component, 2.0 parts by mass of a polymer compound as a fluorine component, and 4000 parts by mass of a solvent component A nitric acid aqueous solution of 1% by mass was used as the acid aqueous solution.

As a metal reagent, a solution (100 mass ppb of metal element concentration) obtained by mixing 1 part by mass of a multi-element mixed standard solution XSTC-622 (10 mg/L of metal element concentration) manufactured by SPEX CertiPrep and 99 parts by mass of propylene glycol monomethyl ether (PGME) was used.

[Preparation of Sample Solution]

99 parts by mass of the polymer composition and 1 part by mass of the solution (100 mass ppb of metal element concentration) as a metal reagent were collected in a container (made of perfluoroalkoxy alkane (PFA) resin, volume 30 mL) that has been acid-cleaned, and mixed with each other to obtain a sample solution (1).

Separately, only the polymer composition was collected in a container (made of perfluoroalkoxy alkane (PFA) resin, volume 30 mL) that has been acid-cleaned, and this was used as a sample solution (2).

[Addition Recovery Test]

By using each of the sample solution (1), the sample solution (2), and the acid aqueous solution, the operations for the following steps (i-1) to (iii-1) was performed in a clean room at room temperature (25° C.).

Step (i-1):

In the container, the acid aqueous solution was added to the sample solution (1) so that the sample solution (1)/the acid aqueous solution=1.0 was obtained in terms of a mass ratio. Next, the container was covered and the sample solution (1) and the acid aqueous solution were stirred with a rotor, and mixed with each other to prepare a dispersion (1).

In another container, the acid aqueous solution was added to the sample solution (2) in the same manner so that the sample solution (2)/the acid aqueous solution=1.0 was obtained in terms of a mass ratio. Next, the other container was covered and the sample solution (2) and the acid aqueous solution were stirred with a rotor, and mixed with each other to prepare a dispersion (2).

Step (ii-1):

The dispersion (1) was centrifuged into a dispersoid layer and a dispersion medium layer using a centrifuge.

Similarly, the dispersion (2) was centrifuged into a dispersoid layer and a dispersion medium layer using a centrifuge. Here, centrifugation was performed under the following conditions.

Centrifugation conditions: rotation speed 2000 rpm, and rotation time 60 minutes Step (iii-1):

Another container (made of perfluoroalkoxy alkane (PFA) resin, volume 30 mL) that has been acid-cleaned was prepared, and into this container, a dispersion medium layer (1) was collected from the dispersion (1) that is separated into the dispersoid layer and the dispersion medium layer.

Similarly, another container (made of perfluoroalkoxy alkane (PFA) resin, volume 30 mL) that has been acid-cleaned was prepared, and into this container, a dispersion medium layer (2) was collected from the dispersion (2) that is separated into the dispersoid layer and the dispersion medium layer.

Next, an inductively coupled plasma mass spectrometry (ICP-MS) was used to quantify the metal elements contained in each of the dispersion medium layer (1) and the dispersion medium layer (2) twice. Here, as a device for the quantification analysis by the ICP-MS, ICP-MS 8900 (manufactured by Agilent Technologies, Inc.) was used.

For each metal element, a recovery rate of each was calculated by the following Expression.

Recovery rate (%)=[(Amount of metal element in dispersion medium layer (1))−(Amount of metal element in dispersion medium layer (2))]/ (Amount of metal element added to sample solution (1))×100

FIG. 1 is a graph showing the results of an addition recovery test.

The vertical axis represents a recovery rate (%). The horizontal axis represents each metal element. Each of the results of the first quantification and the second quantification for one metal element is shown.

The line indicated by "upper" represents that the recovery rate is 100+25(%).

The line indicated by "lower" represents that the recovery rate is 100−25(%).

From FIG. 1, the recovery rate was in a range of 100±25% for any of the metal elements.

Therefore, it can be confirmed that the metal elements were present in the dispersion medium layer.

In addition, the analysis method including steps (i-1) to (iii-1) in the present example was confirmed to be valid (see Guide for Determination of SEMI C10-1109MDL (minimum limit of quantification).

<Analysis Method of Metal Component (1)>

Example 1

The polymer composition was collected in a container (made of perfluoroalkoxy alkane (PFA) resin, volume 30 mL) that has been acid-cleaned, and this was used as a sample solution (2).

Separately, 99.95 parts by mass of the polymer composition and 0.05 part by mass of the solution (100 mass ppb of metal element concentration) as a metal reagent were collected in a container (made of perfluoroalkoxy alkane (PFA) resin, volume 30 mL) that has been acid-cleaned, and mixed with each other to obtain a sample solution (3).

Separately, 99.9 parts by mass of the polymer composition and 0.1 part by mass of the solution (100 mass ppb of metal element concentration) as a metal reagent were collected in a container (made of perfluoroalkoxy alkane (PFA)

resin, volume 30 mL) that has been acid-cleaned, and mixed with each other to obtain a sample solution (4).

Each of the sample solution (2), sample solution (3), sample solution (4), and acid aqueous solution was used to perform the operations for the following steps (i-2) to (iii-2) at room temperature (25° C.) in a clean room.

Step (i-2):

In the container, the acid aqueous solution was added to the sample solution (2) so that the sample solution (2)/the acid aqueous solution=1.0 was obtained in terms of a mass ratio. Next, the container was covered and the sample solution (2) and the acid aqueous solution were stirred with a rotor, and mixed with each other to prepare a dispersion (2).

In another container, the acid aqueous solution was added to the sample solution (3) in the same manner so that the sample solution (3)/the acid aqueous solution=1.0 was obtained in terms of a mass ratio. Next, the other container was covered and the sample solution (3) and the acid aqueous solution were stirred with a rotor, and mixed with each other to prepare a dispersion (3).

In another container, the acid aqueous solution was added to the sample solution (4) in the same manner so that the sample solution (4)/the acid aqueous solution=1.0 was obtained in terms of a mass ratio. Next, the other container was covered and the sample solution (4) and the acid aqueous solution were stirred with a rotor, and mixed with each other to prepare a dispersion (4).

Step (ii-2):

The dispersion (2) was centrifuged into a dispersoid layer and a dispersion medium layer using a centrifuge.

Similarly, the dispersion (3) was centrifuged into a dispersoid layer and a dispersion medium layer using a centrifuge. Similarly, the dispersion (4) was centrifuged into a dispersoid layer and a dispersion medium layer using a centrifuge. Here, centrifugation was performed under the following conditions.

Centrifugation conditions: rotation speed 2000 rpm, and rotation time 60 minutes Step (iii-2):

Another container (made of perfluoroalkoxy alkane (PFA) resin, volume 30 mL) that has been acid-cleaned was prepared, and into this container, a dispersion medium layer (2) was collected from the dispersion (2) that is separated into the dispersoid layer and the dispersion medium layer.

Similarly, another container (made of perfluoroalkoxy alkane (PFA) resin, volume 30 mL) that has been acid-cleaned was prepared, and into this container, a dispersion medium layer (3) was collected from the dispersion (3) that is separated into the dispersoid layer and the dispersion medium layer.

Similarly, another container (made of perfluoroalkoxy alkane (PFA) resin, volume 30 mL) that has been acid-cleaned was prepared, and into this container, a dispersion medium layer (4) was collected from the dispersion (4) that is separated into the dispersoid layer and the dispersion medium layer.

Next, the ICP-MS was used to quantify the metal elements contained in each of the dispersion medium layer (2), dispersion medium layer (3), and dispersion medium layer (4) three times a day for two days (three levels×three times×two days, total n=18). Here, as a device for the quantification analysis by the ICP-MS, ICP-MS 8900 (manufactured by Agilent Technologies, Inc.) was used.

From the results of the above quantification analysis, a detection limit (DL) of each metal element was calculated according to the "Guide for Determination of SEMI C10-1109MDL (minimum limit of quantification)". The results are shown in Table 1 as "Mean MDL (ppt)".

TABLE 1

|  | Mean MDL (ppt) |
| --- | --- |
| Ag | 4 |
| Al | 3 |
| Ca | 5 |
| Cd | 3 |
| Co | 1 |
| Cr | 1 |
| Cu | 2 |
| Fe | 2 |
| Ge | 1 |
| K | 1 |
| Li | 1 |
| Mg | 5 |
| Mn | 1 |
| Mo | 15 |
| Na | 3 |
| Ni | 4 |
| Pb | 1 |
| Sn | 3 |
| Sr | 1 |
| Ti | 2 |
| V | 1 |
| W | 1 |
| Zn | 4 |
| Zr | 1 |

<Analysis Method of Metal Component (2)>

Comparative Example 1

By using each of the sample solution (2), the sample solution (3), and the sample solution (4), the following operation was performed in a clean room at room temperature (25° C.).

In the container that has been acid-cleaned, PGME was added to each of the sample solutions so that PGME/each sample solution was 4.0 in terms of a mass ratio. Next, the container was covered and stirred with a rotor, and each of the sample solutions and PGME were mixed to prepare a dispersion (5), a dispersion (6), and a dispersion (7).

Next, the ICP-MS was used to quantify the metal elements contained in each of the dispersion three times a day for two days (three levels×three times×two days, total n=18). Here, as a device for the quantification analysis by the ICP-MS, ICP-MS 8800 (manufactured by Agilent Technologies, Inc.) was used.

From the results of the above quantification analysis, a detection limit (DL) of each metal element was calculated according to the "Guide for Determination of SEMI C10-1109MDL (minimum limit of quantification)". The results are shown in Table 2 as "Mean MDL (ppt)".

TABLE 2

|  | Mean MDL (ppt) |
| --- | --- |
| Al | 6 |
| Ca | 45 |
| Cr | 58 |
| Cu | 23 |
| Fe | 67 |
| K | 47 |
| Mg | 22 |
| Mn | 22 |
| Na | 91 |
| Ni | 35 |
| Li | 28 |
| Sn | 60 |

TABLE 2-continued

| | Mean MDL (ppt) |
|---|---|
| Zn | 92 |
| Ti | 34 |

From the results shown in Tables 1 and 2, regarding the minimum limit of quantification of aluminum (Al), the lowest limit value that can be quantified was 3 ppt in Example 1, and 6 ppt in Comparative Example 1, and it was confirmed that the most minimum limit capable of being quantified was further lowered by the application of the present invention.

Regarding the metal elements (excluding Al) shown in Table 2, the lowest limit value that can be quantified was in a range of 1 to 5 ppt in Example 1, and 22 to 92 ppt in Comparative Example 1. It was confirmed that by applying the present invention, the most minimum limit capable of being quantified could be further lowered than that of the existing method, and 5 ppt or less of the most minimum limit capable of being quantified could be realized.

In addition, the operations for the steps (i-2) to (iii-2) was performed in a clean room at room temperature (25° C.), and the quantification of the metal elements was performed, except that in the operation for the step (i-2) of the above (Example 1), the mixing ratio of each of the sample solutions (2) to (4) to the acid aqueous solution in terms of a mass ratio is changed to a range of each of sample solutions (2) to (4)/acid aqueous solution=0.80 to 1.25.

From the results of the quantification of such metal elements, a detection limit (DL) of each metal element was calculated according to the "Guide for Determination of SEMI C10-1109MDL (minimum limit of quantification)".

As a result, it was confirmed that even in a case where the mixing ratio of the sample solution to the acid aqueous solution is changed in the range of sample solution/acid aqueous solution=0.80 to 1.25 in terms of a mass ratio, the detection limit (DL) equivalent to that of Example 1 was shown, that is, the most minimum limit capable of being quantified could be made lower than that of the existing method, and 5 ppt or less of the most minimum limit capable of being quantified could be realized.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

What is claimed is:

1. A method of analyzing a metal component contained as an impurity in a polymer composition that contains a polymer and an organic solvent, the method comprising:
   a step (i) of preparing a dispersion consisting of the polymer composition and an acid aqueous solution, wherein the acid in the acid aqueous solution is selected from the group consisting of nitric acid, hydrochloric acid, sulfuric acid, hydrogen fluoride, phosphoric acid, perchloric acid, acetic acid, formic acid, and mixtures thereof;
   a step (ii) of separating the dispersion into a dispersoid layer containing the polymer and a dispersion medium layer containing the metal component; and
   a step (iii) of quantifying the metal component contained in the dispersion medium layer by a method using inductively coupled plasma mass spectrometry (ICP-MS).

2. The method of analyzing a metal component according to claim 1, wherein a mixing ratio of the polymer composition to the acid aqueous solution in the step (i) is the polymer composition/the acid aqueous solution=0.80 to 1.25 in terms of a mass ratio.

3. The method of analyzing a metal component according to claim 1, wherein an operation of the separation in the step (ii) is performed by centrifugation.

* * * * *